United States Patent
Berghofer et al.

(10) Patent No.: US 11,753,526 B2
(45) Date of Patent: Sep. 12, 2023

(54) SYNERGISTICALLY ACTIVE COMPOSITION

(71) Applicant: L. Brüggemann GmbH & Co. KG, Heilbronn (DE)

(72) Inventors: Josef Berghofer, Tauberbischofsheim (DE); Stefan Mark, Bad Rappenau (DE); Stefanie Enderle, Grossbottwar (DE)

(73) Assignee: L. BRÜGGEMANN GMBH & CO. KG, Heilbronn (DE)

( * ) Notice: Subject to any disclaimer, the term of this patent is extended or adjusted under 35 U.S.C. 154(b) by 642 days.

(21) Appl. No.: 16/489,066

(22) PCT Filed: Mar. 5, 2018

(86) PCT No.: PCT/EP2018/055321
§ 371 (c)(1),
(2) Date: Aug. 27, 2019

(87) PCT Pub. No.: WO2018/162399
PCT Pub. Date: Sep. 13, 2018

(65) Prior Publication Data
US 2020/0002508 A1    Jan. 2, 2020

(30) Foreign Application Priority Data
Mar. 6, 2017    (EP) .................................. 17159314

(51) Int. Cl.
| | | |
|---|---|---|
| *C08K 5/41* | (2006.01) | |
| *C08F 2/22* | (2006.01) | |
| *C08F 4/40* | (2006.01) | |
| *C08K 5/1535* | (2006.01) | |
| *C08L 25/14* | (2006.01) | |
| *C08L 33/08* | (2006.01) | |

(52) U.S. Cl.
CPC ................. *C08K 5/41* (2013.01); *C08F 2/22* (2013.01); *C08F 4/40* (2013.01); *C08K 5/1535* (2013.01); *C08L 25/14* (2013.01); *C08L 33/08* (2013.01)

(58) Field of Classification Search
CPC . C08K 5/41; C08K 5/1535; C08F 2/22; C08F 4/40; C08F 6/006; C08L 25/14; C08L 33/08; D06P 5/155; D06P 1/221; D06P 1/62; C07C 313/04; D06L 4/30
See application file for complete search history.

(56) References Cited

U.S. PATENT DOCUMENTS

| | | | |
|---|---|---|---|
| 2014/0000806 A1* | 1/2014 | Han | C08L 23/0861 156/331.7 |
| 2016/0017070 A1* | 1/2016 | Kadir | C08J 3/05 524/561 |
| 2017/0335029 A1* | 11/2017 | Nagano | C08F 6/22 |
| 2020/0002508 A1* | 1/2020 | Berghofer | D06P 1/221 |

FOREIGN PATENT DOCUMENTS

| | | |
|---|---|---|
| EP | 2194079 A1 | 6/2010 |
| WO | 9919067 A1 | 4/1999 |
| WO | 2012/126258 A1 | 9/2012 |
| WO | 2013/113152 A1 | 8/2013 |
| WO | 2013160711 A1 | 10/2013 |

OTHER PUBLICATIONS

International Search Report for International PCT Application No. PCT/EP2018/055321, dated May 7, 2018, 3 pages.
Written Opinion for International PCT Application No. PCT/EP2018/055321, dated May 7, 2018, 6 pages.

* cited by examiner

*Primary Examiner* — Robert S Jones, Jr.
*Assistant Examiner* — Jiangtian Xu
(74) *Attorney, Agent, or Firm* — Saul Ewing LLP; Justin W. Crotty; Dennis Ostrovsky

(57) ABSTRACT

The invention relates to a synergistically active composition which comprises a mixture of a sulfinic acid or a salt thereof and ascorbic acid or a salt thereof and the use of the composition as reducing agent. The reducing power of the composition of the invention is significantly higher than the reducing power of the single components.

5 Claims, No Drawings

SYNERGISTICALLY ACTIVE COMPOSITION

CROSS-REFERENCE TO RELATED APPLICATIONS

This application is the U.S. national phase, pursuant to 35 U.S.C. § 317, of PCT international application Ser. No. PCT/EP2018/055321, filed Mar. 5, 2018, designating the United States and published in English on Sep. 13, 2018 as publication WO 2018/162399 A1, which claims priority under 35 U.S.C. § 119(a) to European patent application No. 17159314.8, filed Mar. 6, 2017. The entire disclosures of the aforementioned patent applications are hereby incorporated herein by reference.

The invention relates to a synergistically active composition which comprises a mixture of a sulfinic acid or a salt thereof and ascorbic acid or a salt thereof and the use of the composition as reducing agent.

BACKGROUND

Formaldehyde sulfoxylates (hydroxymethane sulfinates), in particular sodium formaldehyde sulfoxylate, have proven to be effective and good value reducing agents, in particular in free-radical-initiated emulsion polymerizations. During the reduction process, however, the formaldehyde sulfoxylates eliminate the toxic formaldehyde. Plastics or polymer dispersions which must not contain formaldehyde are polymerized using alternative reducing agents, for example, bisulfites, ascorbic acid, isoascorbic acid or sodium erythrobate. Since these formaldehyde-free reducing agents are weaker reducing agents, the disadvantage of less complete polymerization compared with formaldehyde sulfoxylates has to be accepted. Moreover, an increased coagulate formation or yellowing is observed with said alternative reducing agents.

The disadvantages of the formaldehyde sulfoxylates have been overcome by the sulfinic acid derivatives which additionally have a carboxylic acid group in the molecule. These derivatives are disclosed in WO 99/18067 and because they have a high reducing power and stability and do not release formaldehyde during or after use they are in wide-spread use as reducing agents, in particular in free-radical-initiated emulsion polymerizations. Due to their advantages the sulfinic acid derivatives have already been used in combination with isoascorbic acid to reduce formaldehyde development as described in WO 2013/160711. However, the reducing power of the combination is not fully satisfying.

SUMMARY OF THE INVENTION

The problem underlying the present invention is therefore to provide a reducing agent which exhibits an improved reducing power, in particular in emulsion polymerizations.

This problem has been solved by using a mixture of a sulfinic acid or a salt thereof and ascorbic acid or a salt thereof. It was surprisingly found that this mixture of two reducing agents exhibits a synergistic effect, i.e. the reducing power of the mixture is higher than that of the equivalent amount of the single reducing agents. The reducing power is also surprisingly higher than that one of the mixture of a corresponding sulfinic acid or a salt thereof and isoascorbic acid or a salt thereof.

The invention therefore relates to a composition comprising
a) at least one sulfinic acid of the formula (I)

$$HO-S(-O)_n-\overset{R^1}{\underset{OH}{C}}-R^2 \quad (I)$$

wherein
$R^1$ is H or $C_1$-$C_6$-alkyl,
$R^2$ is —COOH or —$SO_3H$, and
n is 1,
or at least one salt thereof or a mixture of at least one sulfinic acid of formula (I) and at least one salt thereof and
b) ascorbic acid or at least one salt thereof or a mixture of ascorbic acid and at least one salt thereof.

DETAILED DESCRIPTION OF THE INVENTION

In an embodiment, $R^1$ in formula (I) is H or $CH_3$, preferably H.

In a further embodiment, $R^2$ in formula (I) is —COOH.

Particularly preferred compounds of formula (I) are 2-hydroxy-2-sulfinatoacetic acid or 2-hydroxy-2-sulfinatopropionic acid and the salts thereof.

In a further embodiment, the composition comprises the sulfinic acid of formula (I) as a salt. Formula (I) comprises two acidic groups so that the expression "salt" comprises the mono-, di- or mixed salts.

Preferred salts are selected from the group consisting of an alkali metal, alkaline earth metal, zinc, iron and aluminum salt, in particular at least one alkali metal or alkaline earth metal salt such as the sodium or potassium mono- or disalt of 2-hydroxy-2-sulfinatoacetic acid or 2-hydroxy-2-sulfinatopropionic acid.

In another embodiment, the composition comprises a salt of ascorbic acid. A preferred salt is an alkali metal salt such as the sodium or potassium salt.

In another embodiment, the composition comprises a synergistically active amount of components (a) and (b). A synergistic effect is observed over a broad mixing range, i.e. the weight ratio of component (a) to component (b) is in the range of 20:1 to 1:20 or 10:1 to 1:10.

In an embodiment, the weight ratio of component (a) to component (b) is in the range of 5:1 to 1:5, preferably 4:1 to 1:4 and in particular 3:1 to 1:3.

The composition of the invention may be provided as a solid mixture which is storage stable for a long period of time. Even after a storage time of 6 months the reducing power of the composition is substantially unchanged. The water content of the solid mixture is, in general, in the range of 0.1 to 3 wt. %, based on dry solids.

For use the composition may be applied in solid form or as an aqueous solution which may be freshly prepared. For example, the aqueous solution may comprise 5 to 50 wt.-% of the composition, based on the total weight of the composition.

In an embodiment, component (a) additionally comprises the corresponding sulfonate compound or mono-, di- or mixed salt thereof, i.e. the compounds or salts of formula (I), wherein n is 2.

In a further embodiment, component (a) additionally comprises a metal sulfite (the metal is as defined above for the salts of the sulfinic acids of formula (I)).

In a further embodiment, component (a) additionally comprises both, said sulfonate compound or salt thereof and the metal sulfite. Preferably, the composition comprises the sulfonate compound and essentially no metal sulfite ("essentially" means less than 5 wt.-% and preferably less than 1 wt.-%, based on the total weight of component (a).

In a further embodiment, component (a) has the following composition, based on the total weight of component (a):

| | |
|---|---|
| Compound of formula (I) or salt thereof | 20 to 99 wt.-% |
| Sulfonic acid corresponding to formula (I) with n being 2 or salt thereof | 0 to 80 wt.-% |
| metal sulfite | 0 to 40 wt.-%. |

Preferably, component (a) has the following composition, based on the total weight of component (a):

| | |
|---|---|
| Compound of formula (I) or salt thereof | 30 to 60 wt.-% |
| Sulfonic acid corresponding to formula (I) with n being 2 or salt thereof | 40 to 70 wt.-% |
| metal sulfite | 0 to 20 wt.-%. |

In an embodiment, the composition of the invention comprises additional reducing agents such as isoascorbic acid or salts thereof, hydroxymethane sulfonate, acetone bisulfite, a metal hydroxymethane sulfinate (the metal is as defined above for the compound of formula (I)) etc.

In a further embodiment, the composition of the invention comprises conventional additives and auxiliaries, such as other metal salts like a metal sulfate (the metal is as defined above for the metal sulfite).

The amount of additional reducing agents and/or conventional additives and/or auxiliaries is, in general, less than 50 wt. %, based on the total weight of the composition. Thus, the composition of the invention comprises at least 50 wt. %, in particular at least 60 wt. %, of the mixture of components (a) and (b), based on the total weight of the solid mixture.

The composition of the invention can be prepared by mixing the components in the desired mixing ratio.

The compositions of the invention are reducing agents whose reducing power is higher than that of components (a) and (b) taken alone. It is also higher than the reducing power of the mixture of 2-hydroxy-2-sulfinatoacetic acid or salt thereof or isoascorbic acid. They have the further advantage over the conventional formaldehyde sulfoxylate of eliminating no formaldehyde before, during and after use. Furthermore, yellowing is reduced as compared to the use of ascorbic acid alone. The compositions of the invention are thus preferentially used in those fields where a high reducing power is required and the evolution of formaldehyde is to be reduced or even avoided. For example, they can be used as reducing agents in textile printing, in particular in textile discharge printing, in textile bleaching or vat dyeing, or as reducing agents for bleaching minerals, such as kaolin etc., and fibers, for example cellulose fibers. They are preferably used, however, as initiator in emulsion polymerization together with peroxidic initiators in order to allow the polymerization to be carried out at a lower temperature. For this purpose, the compositions of the invention may, if desired, be also used together with oxidizable metal ions, such as $Fe^{2+}$, $Mn^{2+}$ etc. Preferably, the compositions of the invention are used as reducing agents in the post-polymerization of an emulsion polymer in order to reduce the residual monomer content to an acceptable level.

The compositions of the invention can be used in any type of emulsion polymerisations and for the polymerization of any monomers that are used in emulsion polymers. Preferably, they are used in polymerisations where $C_1$-$C_{18}$ alkyl esters of α,ß-unsaturated carboxylic acids, vinyl aromatic compounds or vinyl esters of carboxylic esters are homo- or copolymerized.

Examples of suitable $C_1$-$C_{18}$ alkyl esters of α,ß-unsaturated carboxylic acids are the esters of acrylic acid, methacrylic acid, crotonic acid, isocrotonic acid, maleic acid, fumaric acid etc. the ester group is preferably a $C_1$-$C_8$ alkyl such as methyl, ethyl, n-butyl, ethylhexyl, etc.

Suitable comonomers in the polymerization of $C_1$-$C_{18}$ alkyl esters of α,ß-unsaturated carboxylic acids are, for example, vinyl aromatic compounds such as styrene, α,ß-unsaturated carboxylic acids such as acrylic acid or methacrylic acid, vinyl esters of carboxylic esters such as vinyl acetate, (meth)acrylonitrile, (meth)acryl amide, hydroxyalkyl esters of α,ß-unsaturated carboxylic acids such as hydroxyethylester of (met)acrylic acid.

Vinyl aromatic compounds are, for example, styrene, 4-methylstyrene, etc. Suitable comonomers are $C_1$-$C_{18}$ alkyl esters of α,ß-unsaturated carboxylic acids as mentioned above, butadiene, etc.

Vinyl esters of carboxylic esters are, for example, vinyl esters with $C_1$-$C_{18}$ carboxylic acids such as acetic acid etc. Suitable comonomers are $C_1$-$C_{18}$ alkyl esters of α,ß-unsaturated carboxylic acids as mentioned above, butadiene, styrene, ethylene, propylene, etc.

EXAMPLES

The examples below illustrate the invention without limiting it. All percent values are % by weight (wt. %).

To demonstrate the synergistic effect of the compositions of the invention a styrene-n-butylacrylate latex (Liocryl XAS 4727 obtained from Synthopol Chemie GmbH & Co. KG) was used. Styrene and n-butylacrylate monomers were added to the latex to a final content of 5000 ppm each and homogenized to obtain a latex emulsion of pH 4.5. 350 g of the latex were charged into a vessel and the temperature thereof was regulated to 65° C. using a thermostat with stirring. The following mixtures of reducing agents given in table 1 below were prepared:

TABLE 1

| | TP 1328 (%) | Sodium ascorbat (%) | Sodium isoascorbat (%) |
|---|---|---|---|
| RM 1 | 50 | 50 | — |
| RM 2 | 50 | — | 50 |
| RM 3 | 100 | — | — |
| RM 4 | — | 100 | — |
| RM 5 | — | — | 100 |
| RM 6 | 25 | 75 | — |
| RM 7 | 75 | 25 | — |

RM: Reduction agent mixture
TP 1328: Sodium salt of 2-hydroxy-2-sulfinatoacetic acid containing 55% of the sodium salt of 2-hydroxy-2-sulfonatoacetic acid Each of these mixtures was added in a separate experiment to the latex at 65° C. and pH 4.5 in an amount of 0.05 wt. %, based on the total weight of the latex. Simultaneously, the oxidation agent, tert.-butylhydroperoxide (tBHP), was added to the latex at 65° C. in an amount of 0.1 wt. %, based on the total weight of the latex. The addition rate and the concentration of the reducing agent mixtures and of the oxidation agent is given in table 2 below:

TABLE 2

|  | Amount to be added in 60 min | Amount to be added in 15 min | Addition rate |
|---|---|---|---|
| 2.0% RM solution (5 g RM per 250 mL water) | 8.75 mL | 2.19 mL | 0.146 mL/min |
| 2.2% oxidation agent (5.5 g tBHP (70%) per 250 mL water) | 22.72 mL | 5.76 mL | 0.378 mL/min |

Samples were taken from the flask at times 0, 15 min, 30 min, 45 min and 60 min and the reaction in the samples was terminated by adding 10 mg MEHQ (2-methoxyphenol). The residual monomer content was then determined as follows:

A Headspace-GC-MS of Perkin Elmer with Headspace-Autosampler and the Multiple Headspace Extraction method were used for determining the residual monomer content. The results for residual n-butylacrylate and styrene are given in the following tables 3 to 9.

TABLE 3 residual monomer content after use of RM1

|  | Monomer content n-butylacrylate | Monomer content styrene |
|---|---|---|
| sample 0 (after 0 min) | 100.0% | 100.0% |
| sample 1 (after 15 min) | 49.9% | 38.5% |
| sample 2 (after 30 min) | 26.8% | 16.9% |
| sample 3 (after 45 min) | 15.0% | 6.8% |
| sample 4 (after 60 min) | 7.9% | 2.2% |

TABLE 4 residual monomer content after use of RM2

|  | Monomer content n-butylacrylate | Monomer content styrene |
|---|---|---|
| sample 0 (after 0 min) | 100.0% | 100.0% |
| sample 1 (after 15 min) | 53.9% | 42.8% |
| sample 2 (after 30 min) | 31.0% | 19.3% |
| sample 3 (after 45 min) | 19.0% | 8.9% |
| sample 4 (after 60 min) | 11.5% | 4.0% |

TABLE 5 residual monomer content after use of RM3

|  | Monomer content n-butylacrylate | Monomer content styrene |
|---|---|---|
| sample 0 (after 0 min) | 100.0% | 100.0% |
| sample 1 (after 15 min) | 59.2% | 43.2% |
| sample 2 (after 30 min) | 30.0% | 17.5% |
| sample 3 (after 45 min) | 18.1% | 7.3% |
| sample 4 (after 60 min) | 11.0% | 3.3% |

TABLE 6 residual monomer content after use of RM4

|  | Monomer content n-butylacrylate | Monomer content styrene |
|---|---|---|
| sample 0 (after 0 min) | 100.0% | 100.0% |
| sample 1 (after 15 min) | 76.5% | 67.3% |
| sample 2 (after 30 min) | 41.8% | 27.5% |
| sample 3 (after 45 min) | 23.8% | 12.0% |
| sample 4 (after 60 min) | 15.1% | 6.0% |

TABLE 7 residual monomer content after use of RM5

|  | Monomer content n-butylacrylate | Monomer content styrene |
|---|---|---|
| sample 0 (after 0 min) | 100.0% | 100.0% |
| sample 1 (after 15 min) | 67.3% | 57.9% |
| sample 2 (after 30 min) | 36.2% | 22.9% |
| sample 3 (after 45 min) | 18.9% | 9.7% |
| sample 4 (after 60 min) | 10.1% | 3.8% |

TABLE 8 residual monomer content after use of RM6

|  | Monomer content n-butylacrylate | Monomer content styrene |
|---|---|---|
| sample 0 (after 0 min) | 100.0% | 100.0% |
| sample 1 (after 15 min) | 46.1% | 39.0% |
| sample 2 (after 30 min) | 25.4% | 16.1% |
| sample 3 (after 45 min) | 14.0% | 5.3% |
| sample 4 (after 60 min) | 5.7% | 1.4% |

TABLE 9 residual monomer content after use of RM7

|  | Monomer content n-butylacrylate | Monomer content styrene |
|---|---|---|
| sample 0 (after 0 min) | 100.0% | 100.0% |
| sample 1 (after 15 min) | 48.4% | 40.9% |
| sample 2 (after 30 min) | 26.5% | 15.8% |
| sample 3 (after 45 min) | 15.9% | 7.0% |
| sample 4 (after 60 min) | 8.9% | 2.5% |

The tables show that the residual monomer content for the compositions of the invention is well below the additive values for the single components, see table 3 as compared to tables 5 and 6. Furthermore, a comparison of tables 3 and 4 shows that the compositions of the invention have a higher reducing power than the composition comprising isoascorbic acid in place of ascorbic acid. This is highly surprising when considering that isoascorbic acid has a higher reducing power than ascorbic acid, see tables 6 and 7. Consequently, one would expect the reducing power of a composition comprising a sulfonate compound of formula (I) and ascorbic acid being lower than that of a composition comprising isoascorbic acid in place of ascorbic acid. By contrast, however, the reducing power is actually increased in the compositions of the invention.

The invention claimed is:

1. A composition comprising a weight ratio of component (a) to component (b) in the range of 3:1 to 1:3, wherein component (a) has the following composition, based on the total weight of component (a):

30 to 60 wt. % of a sodium salt of 2-hydroxy-2-sulfinatoacetic acid;

40 to 70 wt. % of a sulfonic acid of formula (I), a sodium salt thereof, or a mixture thereof;

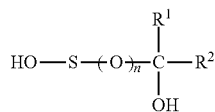

(I)

wherein
R$^1$ is H,
R$^2$ is —COOH; and
n is 2,
0 to 20 wt. % of metal sulfite; and
component (b) is sodium ascorbate;
wherein the sodium salt of the sulfonic acid of formula (I) is the sodium salt of 2-hydroxy-2-sulfonatoacetic acid; and the sodium salt of 2-hydroxy-2-sulfonatoacetic acid is about 55 wt. % of component (a).

2. The composition of claim 1 being in the form of an aqueous solution or suspension.

3. The composition of claim 1 being in the form of a solid mixture.

4. The composition of claim 3, comprising at least 50 wt. % of a mixture of components a) and b), based on the total weight of the solid mixture.

5. The composition of claim 4 comprising at least 60 wt. % of the mixture of components (a) and (b), based on the total weight of the solid mixture.

* * * * *